United States Patent
Yang

(10) Patent No.: US 10,716,829 B2
(45) Date of Patent: Jul. 21, 2020

(54) METHOD AND COMPOSITION FOR TREATMENT OF HAIR LOSS

(71) Applicant: NATIONAL HEALTH RESEARCH INSTITUTES, Zhunan Town, Miaoli County (TW)

(72) Inventor: Liang-Tung Yang, Zhunan Town, Miaoli County (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 0 days.

(21) Appl. No.: 15/763,356

(22) PCT Filed: Sep. 26, 2016

(86) PCT No.: PCT/US2016/053702
§ 371 (c)(1),
(2) Date: Mar. 26, 2018

(87) PCT Pub. No.: WO2017/053939
PCT Pub. Date: Mar. 30, 2017

(65) Prior Publication Data
US 2018/0271936 A1    Sep. 27, 2018

Related U.S. Application Data

(60) Provisional application No. 62/233,354, filed on Sep. 26, 2015.

(51) Int. Cl.
| | |
|---|---|
| *A61K 38/18* | (2006.01) |
| *C07K 14/475* | (2006.01) |
| *A61K 38/17* | (2006.01) |
| *A61K 8/64* | (2006.01) |
| *A61Q 7/00* | (2006.01) |
| *A61K 8/66* | (2006.01) |
| *A61P 17/14* | (2006.01) |
| *A61K 9/00* | (2006.01) |
| *A61K 38/45* | (2006.01) |

(52) U.S. Cl.
CPC .............. *A61K 38/177* (2013.01); *A61K 8/64* (2013.01); *A61K 8/66* (2013.01); *A61K 9/0014* (2013.01); *A61K 38/1709* (2013.01); *A61K 38/18* (2013.01); *A61K 38/45* (2013.01); *A61P 17/14* (2018.01); *A61Q 7/00* (2013.01); *C07K 14/475* (2013.01); *C12Y 204/01221* (2013.01)

(58) Field of Classification Search
CPC .............. A61K 38/177; A61K 38/1709; A61K 38/179; A61K 38/18; C07K 14/705; C07K 14/475
See application file for complete search history.

(56) References Cited

U.S. PATENT DOCUMENTS

| 5,786,158 A * | 7/1998 | Artavanis-Tsakonas .................... A61K 31/70 435/7.1 |
| 2002/0151487 A1 | 10/2002 | Nickoloff et al. |
| 2006/0177479 A1 * | 8/2006 | Giachelli ............... A61K 38/17 424/426 |

FOREIGN PATENT DOCUMENTS

WO    WO 2012/035309 A1    3/2012

OTHER PUBLICATIONS

Ambler et al. Expression of Notch pathway genes in mammalian epidermis and modulation by beta-catenin. Developmental Dynamics 236: 1595-1601, 2007.*
Estrach et al. Jagged 1 is a beta-catenin target gene required for ectopic hair follicle formation in adult epidermis. Development 133: 4427-4438, 2006.*
Estrach et al. Role of the Notch ligand Delta1 in embryonic and adult mouse epidermis. J Invest Dermatol 128: 825-832, 2008.*
Santos et al. Drug discovery for alopecia: gone today, hair tomorrow. Expert Opin Drug Discovery 10(3): 269-292, published online Feb. 9, 2015.*
Uyttendaele et al. Activation of Notch1 in the hair follicle leads to cell-fate switch and Mohawk alopecia. Differentiation 72: 396-409, 2004.*
Yamamoto et al. Notch/RBP-J signaling regulates epidermis/hair fate determination of hair follicular stem cells. Current Biol 13: 333-338, 2003.*
Lin et al. Jagged1 and epidermal growth factor promoted androgen-suppressed mouse hair growth in vitro and in vivo. Frontiers Pharmacol 10: 1634, 2020 (12 total pages).*
Lin et al. "Notch signaling regulates late-stage epidermal differentiation and maintains postnatal hair cycle homeostasis" PLoS One. Jan. 18, 2011, vol. 6 No. 1, pp. 1-19.

* cited by examiner

*Primary Examiner* — Bridget E Bunner
(74) *Attorney, Agent, or Firm* — Muncy, Geissler, Olds & Lowe, P.C.

(57) ABSTRACT

A method of treating a hair loss condition, comprising administering a Notch signaling pathway activator to a subject in need thereof.

4 Claims, 14 Drawing Sheets

A

B

A

B

A

B

METHOD AND COMPOSITION FOR TREATMENT OF HAIR LOSS

CROSS-REFERENCE TO RELATED APPLICATION

This application claims priority to U.S. Provisional Application No. 62/233,354, filed on Sep. 26, 2015, the entire content of which is hereby incorporated by reference herein in its entirety.

BACKGROUND

Adult stem cells maintain tissue homeostasis and regeneration throughout the animal's lifetime. The murine hair follicle offers a model system for studying the mechanism of tissue regeneration. The hair follicle consists of three regions: the lower segment (bulb), the middle segment (bulge and isthmus), and the upper segment (infundibulum). After initial morphogenesis, the lower segment of hair follicles undergo repeated cycles of catagen (regression phase), telogen (resting phase), and anagen (proliferation phase). Underpinning this regenerative cycle is the multipotent and self-renewal capability of hair follicle stem cells (HFSCs), which reside in a specialized niche called the bulge.

In telogen, both bulge stem cells (Bu-SCs) and secondary hair germ (Hg), a small cluster of cells beneath the bulge, are quiescent. Hg directly adjoins a population of mesenchymal cells, called the dermal papillae (DP). At anagen onset, Hg becomes activated prior to Bu-SCs by responding to cues from the DP and surrounding microenvironment. Proliferative Hg then generates the hair matrix, the transit-amplifying cells (TACs) of hair follicles, which has distinct molecular signatures from that of Bu-SCs/Hg. Matrix cells proliferate and progress to differentiate into the hair shaft and inner root sheath (IRS) during anagen. In contrast to Hg, Bu-SCs become activated 1-2 days later in anagen to make the extending outer root sheath (ORS) and to self-renew briefly for replenishing the expended HFSCs. In catagen, the hair progeny (matrix, lower ORS) apoptoseses and the remaining epithelial strand retracts upward together with the DP. At catagen/telogen transition, some upper ORS cells that survive catagen form the new bulge and hair germ being used for the next hair cycle.

In mammals, four Notch receptors (Notch1-4) and five canonical Notch ligands (Jagged1-2, Delta1, 3, and 4) have been identified. Notch ligand-receptor interactions between contacting cells lead to serial proteolysis of the Notch receptor to generate Notch intracellular domain (NICD). NICD translocates into the nucleus and binds to Rbpj and Mastermind, thereby activating the downstream effectors, including the Hes and Hey gene family of transcriptional repressors. Notch signaling is modulated by glycosylation of the extracellular domain of Notch receptors. One of the modifiers is protein O-fucosyltransferase 1 (Pofut1), which transfers O-fucose to a particular consensus sequence in the EGF-like repeats of Notch receptor extracellular domain and is ubiquitously expressed in mammalian tissues. Biochemical studies demonstrated that O-fucose modification of mammalian Notch receptors is required for efficient ligand-receptor binding and subsequent signal transduction. Loss of Pofut1 in the mouse embryo resulted in a severe phenotype similar to that of embryos lacking core components of Notch signaling pathway, such as Presenilins and Rbpj.

Expression patterns of Notch ligands, receptors, and downstream effectors in embryonic and adult skin are in a complex and dynamic manner (Watt F M et al., Curr Opin Cell Biol 20:171-179, 2008). Loss and gain-of-function animal studies revealed that canonical Notch-Rbpj signaling axis acts as a commitment switch at the basal/spinous layer (Blanpain C et al., Genes Dev 20:3022-3035, 2006). Loss of Notch signaling does not affect hair follicle patterning or hair placode formation; however, Notch signaling is required for complete differentiation of the hair follicle (Blanpain C et al., Genes Dev 20:3022-3035, 2006). Interestingly, epithelial deletion of Notch1 or Notch ligand Delta1 caused defects in anagen phase of the first hair cycle, suggesting that Notch signaling may play a role in the hair cycle regulation.

The basic helix-loop-helix (bHLH) gene Hes1 is an important effector mediating context-dependent function of Notch signaling in a variety of tissue types. Hes1 has been involved in the maintenance of stem/progenitors cells in nervous and digestive system by negatively regulating tissue-specific bHLH activators. Moreover, Hes1 is expressed in the spinous keratinocytes and required for maintaining the progenitor fate of spinous cells via regulating Ascl2, a bHLH transcriptional activator, during epidermal development. Interestingly, Hes1-null epidermis developed normally when transplanted to adult mice, suggesting a restricted role of Hes1 in developmental stages. Hes1 is expressed at low levels in telogen hair follicles, and its expression is increased in growing hair follicles. However, the exact function of Hes1 in the hair cycle and its role in the maintenance of the hair follicle stem/progenitor cells are less understood.

SUMMARY

In one aspect, described herein is a method of treating a hair loss condition, comprising administering a Notch signaling pathway activator to a subject in need thereof. The hair loss condition can be male-pattern hair loss, female-pattern hair loss, alopecia areata, anagen effluvium, or telogen effluvium.

In one embodiment, the Notch signaling pathway activator is a Notch ligand. For example, the ligand can be Jagged1, Jagged2, Delta1, or Delta4.

In another embodiment, the Notch signaling pathway activator is a Notch downstream effector, e.g., Hes1.

The Notch signaling pathway activator is a Notch modifier in one embodiment of the treatment method. One exemplary Notch signaling pathway activator is protein O-fucosyltransferase 1 (Pofut1).

The Notch signaling pathway activator can be administered to the subject locally to an area affected with hair loss.

In another aspect, described herein is a composition for use in treating a hair loss condition. The composition contains an effective amount of a Notch signaling pathway activator and a physiologically acceptable carrier. The composition can be used in the treatment method described herein.

In one embodiment, the composition is a topical formulation. For example, the formulation can be a cream, emulsion, lotion, ointment, foam, liquid, paste, suspension, aerosol, spray, powder, or patch.

The details of one or more embodiments are set forth in the accompanying drawing and the description below. Other features, objects, and advantages of the embodiments will be apparent from the description and drawing, and from the claims.

DETAILED DESCRIPTION

Figure 1:
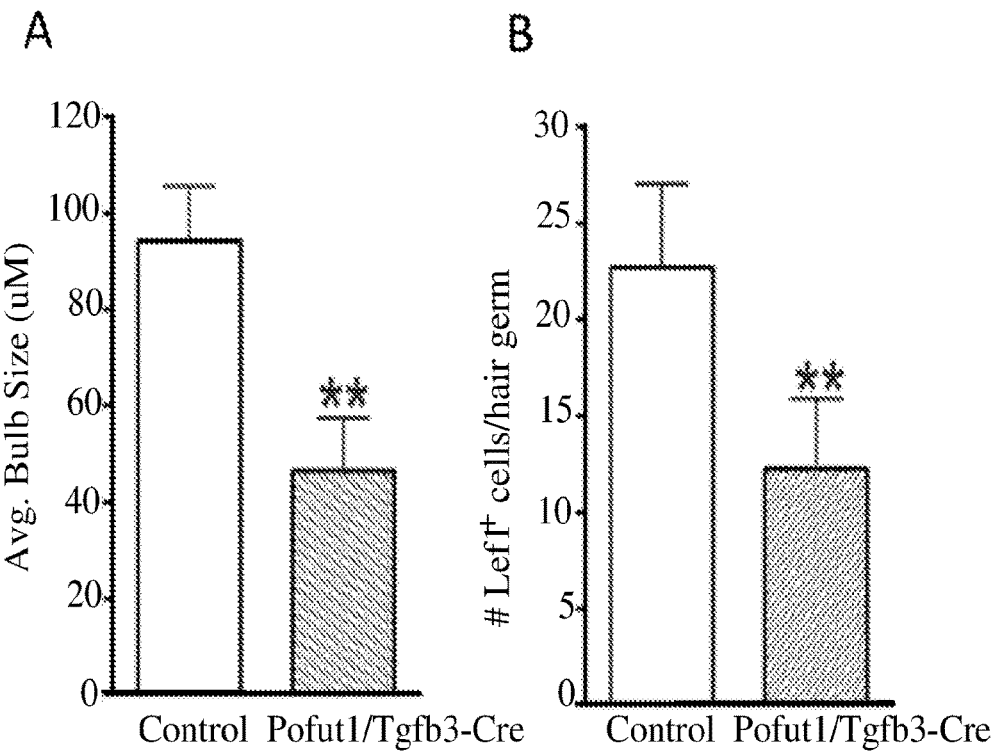
FIGS. 1A-IC are a set of graphs showing that inactivation of Pofut1 in hair follicle lineages resulted in a defect in anagen re-entry. Back skin samples from control and Pofut1/Tgfb3-Cre mice at P30 were immunostained for Ki67. Back skin samples from control and Pofut1/Tgfb3-Cre mice at P22 (telogen) and P24 (early anagen) were immunostained for Lef1, double-stained for Lef1 and α6-integrin (α6), double-stained for P-cadherin (Pcad) and CD34, and double-stained for Pcad and Ki67, (A) The size of hair bulbs from control and Pofut1/Tgfb3-Cre mice at P30 was quantified. The bar diagram shows the length of hair bulbs (mean+/−s.d., n=30) from two independent control and mutant pairs, : P<0.01. (B) and (C) Lef1-positive (Lef1$^+$) and Ki67-positive (Ki67$^+$) cells in the hair germ from control and Pofut1/Tgfb3-Cre mice at P24 were quantified. The bar diagrams show the number of Lef1$^+$ cells (B) and Ki67$^+$ cells (C) per hair germ (mean+/−s.d, n=60) from two independent control and mutant pairs, :P<0.01. Antibodies used were color-coded according to fluorophore-tagged secondary antibodies.
Figure 1:
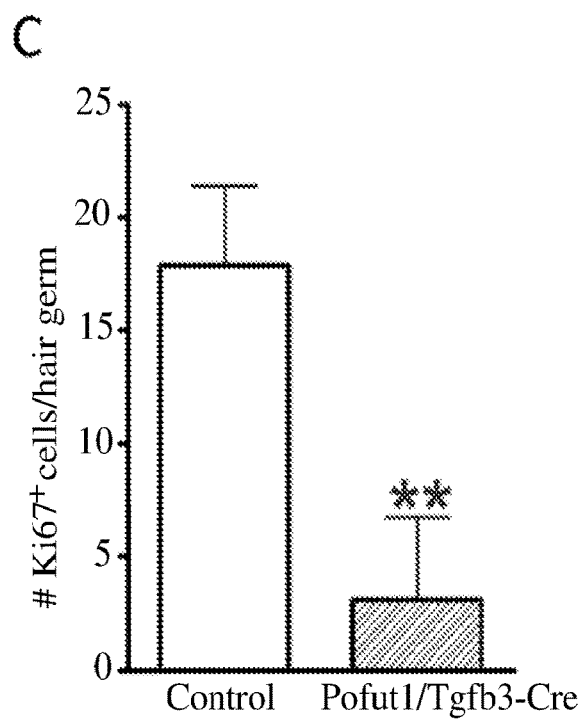

It was unexpectedly discovered that Notch signaling is crucial for the self-renewal and long-term regeneration of HFSCs. Therefore, described herein is a method for treating hair loss using an agent that activates the Notch signaling pathway.

A Notch signaling pathway activator can be, for example, a Notch ligand. A Notch ligand is an agent that can bind and activate a Notch receptor. The ligand can be Jagged1, e.g., NCBI Accession # AF003837 (Homo sapiens), BC058675 (Mus musculus), or NM 019147 (Rattus norvegicus), Jagged2, e.g., NCBI Accession # AF029778 (Homo Sapiens), AF038572 (Mus musculus), or U70050 (Rattus norvegicus), Delta1, e.g., NCBI Accession # AF222310 (Homo sapiens), BC065063 (Mus musculus), or U78889 (Rattus norvegicus), or Delta4, e.g., NCBI Accession # NM_019074 (Homo sapiens), BC042497 (Mus musculus), or NM_001107760 (Rattus norvegicus). The ligand can also be a functional variant (e.g., a mutant) or functional fragment of a wild-type ligand. The ligand can also be a modified (e.g., pegylated), fusion, or chimeric molecule that contains a wild-type Notch ligand, a functional variant thereof, or a functional fragment thereof. Various Notch ligands that are fragments of Jagged1, Jagged2, Delta1, or Delta4 are known in the art.

Alternatively, the Notch signaling pathway activator can be a Notch downstream effector such as Hes1, e.g., NCBI Accession # BC039152 (Homo sapiens), BC051428 (Mus musculus), or BC061730 (Rattus nirvegicus). The Notch downstream effector can be a functional variant (e.g., a mutant) or functional fragment of a wild-type protein. The Notch signaling pathway activator can also be a modified (e.g., pegylated), fusion, or chimeric molecule that contains a wild-type Notch effector, a functional variant thereof, or a functional fragment thereof.

The Notch signaling pathway activator can also be a modifier of Notch receptor, such as protein O-fucosyltransferase 1 (Pofut1), e.g., NCBI Accession # BC000582 (Homo sapiens), BC046295 (Mus musculus), or NM_001002278 (Rattus norvegicus). The Notch signaling pathway activator can be a functional variant (e.g., a mutant) or functional fragment of a wild-type Pofut1. The Notch signaling pathway activator can also be a modified, fusion, or chimeric molecule that contains a wild-type Notch modifier, a functional variant thereof, or a functional fragment thereof.

The above-mentioned Notch signaling pathway activators can be obtained using methods known in the art, e.g., recombinant techniques, or from publically available sources.

To treat hair loss in a subject, a Notch signaling pathway activator is administered to the subject. The term "hair loss", "alopecia" or "baldness," as used herein, refers to a loss or lack of hair at a part of the head or body. Hair loss conditions include male-pattern hair loss, female-pattern hair loss, alopecia areata, anagen effluvium, and a thinning of hair known as telogen effluvium. Alopecia areata causes patches of baldness about the size of a large coin. Anagen effluvium is widespread hair loss that can affect the scalp, face and body. One of the most common causes of this type of hair loss is chemotherapy for cancer treatment. The term "hair" as used herein does not refer to inner ear hair.

The Notch signaling pathway activator can be administered to a subject via various routes, e.g., oral, parenteral, intravenous, intramuscular, subcutaneous, topical or transdermal routes.

Also described herein is a composition for treating a hair loss condition. The composition includes an effective amount of a Notch signaling pathway activator and a physiologically acceptable carrier. The carrier must be "acceptable" in the sense that it is compatible with the active ingredient of the composition and is not deleterious to the subject to be treated. The carrier is selected on the basis of the mode and route of administration and standard pharmaceutical practice.

In one embodiment, the composition is formulated as a topical composition that can be applied locally to an area affected by hair loss. A topical formulation can include one or more carriers to formulate the composition in a particular form (e.g., cream), or to enhance the feel, color, scent, absorbability, or spreadibility of the composition. The topical composition for treating hair loss can include ingredients that may be found in a cosmetic formulation, such as pigments, fragrances, preservatives, protectives, adsorbents, demulcents, emollients, buffering agents, skin-penetration agents, and surfactants. The topical composition can also contain one or more skin care ingredients, e.g., vitamins or oils.

Formulations suitable for transdermal administration can be presented as discrete patches, as in a reservoir or microreservoir system, adhesive diffusion-controlled system or a matrix dispersion-type system.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are herein incorporated by reference in their entirety.

EXAMPLES

Example 1: Ablation of Notch Signaling in Hair Follicle Lineages Causes a Delay in Anagen Re-Entry Previous studies on the role of Notch signaling in hair follicle cycling using Rbpj deletion by Krt14-Cre deleter line resulted in neonatal death due to severe epidermal barrier function defect. To circumvent the neonatal lethality caused by ablation of Notch signaling in the basal epidermis, we used Tgfb3-Cre deleter line to ablate Potfu1 in the suprabasal epidermis and the hair follicle lineage (Lin H Y et al., PLoS One 6:e15842, 2011).

Generation of Tgfb3-Cre (Tgfb3-Cre$^{+/wt}$), floxed Pofut1 (Pofut1$^{fx/fx}$), and floxed Hes1 (Hes1$^{fx/fx}$) mice has been described previously (Shi S, Stanley P., Proc Natl Acad Sci USA 100:5234-5239, 2003; Yang L T, Li W Y, Kaartinen V. 2008. Tissue-specific expression of Cre recombinase from the Tgfb3 locus. Genesis 46:112-118.; Imayoshi I et al., Development 135:2531-2541, 2008). Pofut1$^{fx/fx}$ mice were crossed with Tgfb3-Cre mice to generate heterozygous Tgfb3-Cre$^{+/wt}$; Pofut1$^{fx/wt}$ mice, which were then crossed with Pofut1$^{fx/fx}$ mice to create Pofut1$f^{fx/fx}$; Tgfb3-Cre conditional knockout mice (hereafter named Potfu1/Tgfb3-Cre). Age-matched Pofut1$^{fx/fx}$ or Pofut1$^{fx/wt}$ mice were used as littermate controls. Pofut1/Tgfb3-Cre mice had an average life span of 4-5 months and exhibited progressive alopecia in a head-to-tail direction after 3 weeks postpartum.

All animal work was conducted according to Taiwan COA national guidelines. All studies and procedures performed on mice were carried out at the research laboratory of the National Health Research Institutes (NHRI) and were approved by the NHRI Animal Care and Use Committee.

Lower back skin samples were fixed with 4% paraformaldehyde either for 30 min on ice followed by processing for frozen sectioning, or for 4 h at room temperature followed by processing for paraffin sectioning. All samples were sectioned at 7 µm. For histology, sections were stained with Hematoxylin and Eosin using standard procedures.

Histological analysis revealed that Pofut1/Tgfb3-Cre mice displayed smaller hair follicles than those of control mice at P30. Therefore, back skin sections from control and mutant mice were immunostained for Ki67, a proliferating nuclear antigen, to examine the hair bulb. We found a decrease in both the Ki67-positive matrix cells and the size of the hair bulb in mutant hair follicles at P30 (FIG. 1, A). The size reduction of hair bulbs seen in mutant mice suggested an impairment of progenitor activation or an increase of cell apoptosis in the bulb matrix cells. We further investigated these two possibilities.

The hair germ, which is a distinct epithelial structure separating the bulge from the dermal papilla, directly contributes to the follicular lineages of the next hair cycle. To examine the status of hair germ between control and Pofut1/Tgfb3-Cre mice, back skin samples at P22 (telogen) and P24 (early anagen) were analyzed for hair germ markers (Lef1 and P-cadherin) and proliferation status. While the size of hair germs (Lef1$^+$ and Pcad$^+$ cells) was comparable between control and mutant mice at anagen, mutant hair follicles displayed smaller hair germs with fewer Lef1$^+$ positive cells than control hair follicles at early anagen (FIG. 1, B). In addition, double staining for P-cadherin and Ki67 revealed a reduction in the numbers of Ki67$^+$ cells in mutant hair germs compared to control hair germs at P24 (FIG. 1, C). These data collectively suggest that Notch signaling loss leads to a defect in anagen re-entry.

Example 2: Notch Signaling Regulates Proper Proliferation and Cell Death of Hair Follicle Stem Cells/Progenitors During the Hair Follicle Cycling Next, we investigated the underlying mechanism of the smaller bulge/hair germ seen in Pofut1/Tgfb3-Cre mice by analyzing the proliferation and apoptosis status during the hair cycle.

Figure 2:
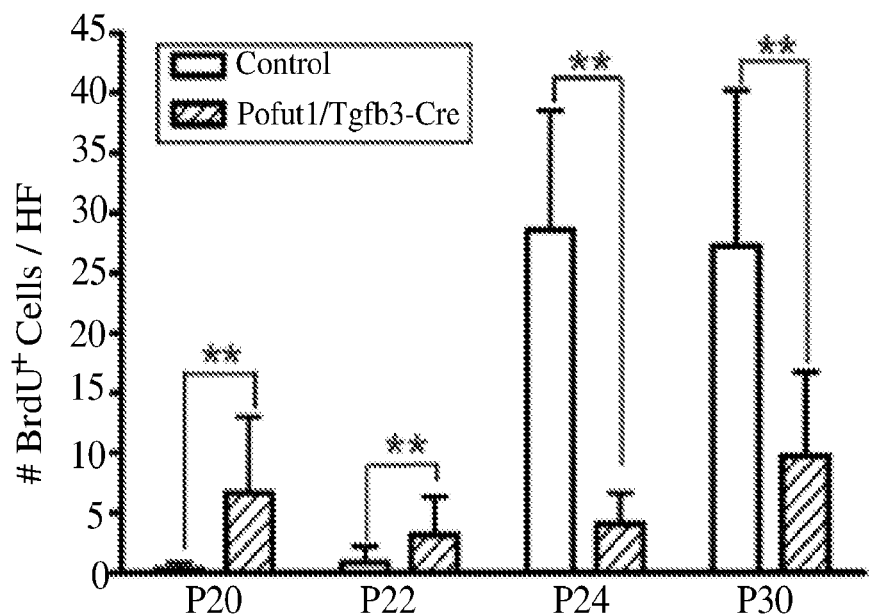
FIGS. 2A-2B are a set of graphs showing that ablation of Pofut1 in hair follicle lineages resulted in dysregulation of proliferation and apoptosis during the hair cycle transition, (A) Control and Pofut1/Tgfb3-Cre mice were labeled with BrdU at P20 (catagen), P22 (telogen), P24 (early anagen), and P30 (late anagen). Back skin samples at stages indicated were double-stained for BrdU and vimentin. Immunostaining of vimentin was used to label the DP in sections and to exclude the misangled follicles in analyses. BrdU-positive (BrdU$^+$) cells in were quantified. The bar diagram shows the number of BrdU cells per hair follicle (mean+/−s.d., n>40) at stages indicated from two to three independent control and mutant pairs. (B) Continuous serial sections of above-described samples were immunostained for cleaved Caspase-3. Cells staining positive for cleaved Caspase3 were quantified. The bar diagram shows the number of cleaved Caspase3-positive (apoptotic) cells per hair follicle (mean+/−s.d., n>40) at stages indicated from two to three independent control and mutant pairs, *: P<0.05, **:: P<0.01.
Figure 2:
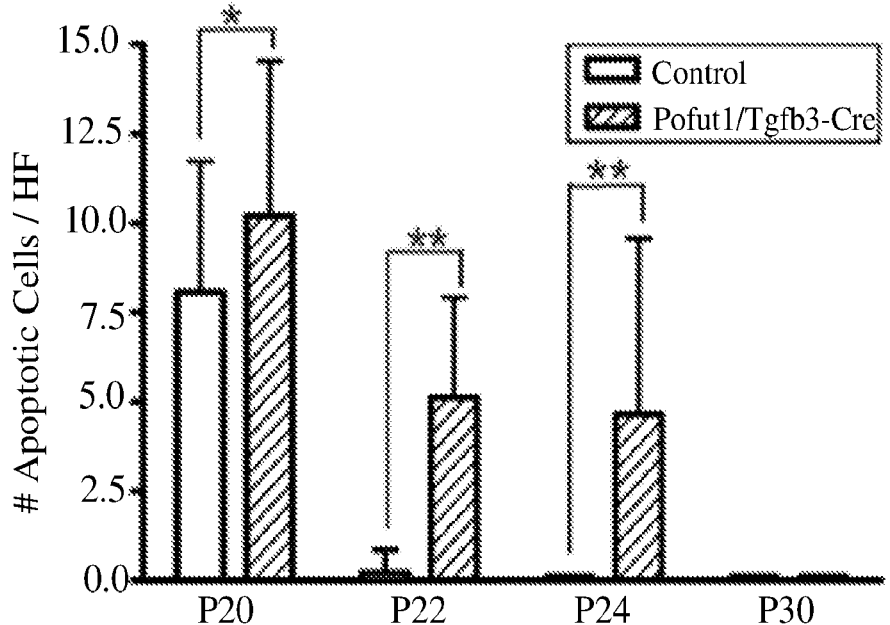

Control and Pofut1/Tgfb3-Cre mouse pairs were BrdU-labeled at different hair cycle stages (from catagen to late anagen) and immunostained for BrdU. Cell proliferation in the hair germ at P24 (early anagen) and in the hair bulb at P30 (late anagen) was largely reduced in mutant hair follicles compared with control samples, as revealed by BrdU staining and quantitative analysis (FIG. 2, A). Notably, BrdU staining was observed in the regressing ORS (at P20 catagen) as well as in the bulge/isthmus region (at P22 telogen) of mutant hair follicles.

The continuous serial sections used in the cell proliferation assay were also immunostained for apoptosis marker cleaved Caspase-3. For immunostaining, fixed sections were blocked in blocking solution (5% normal goat serum, 2.5% bovine serum albumin, and 0.3% Triton-X 100 in PBS), and incubated with primary antibodies in blocking solution overnight at 4° C. After washing, sections were incubated with Dylight 488- or Dylight 594-conjugated secondary antibodies (Jackson ImmunoResearch) and counterstained with DAPI in mounting media (Vector Labs). Images were taken using an Olympus DP71 CCD device attached to an Olympus BX51 microscope with DP controller and DP manager software or using a Leica TCS SP5 confocal microscope system with Leica Power 3D software. Identical conditions of exposure and background balance for image capture were used for comparisons between control and mutant samples. Similar results were obtained with at least three independent sets of control and mutant pairs.

Control hair follicles exhibited positive staining in the regressing ORS only at P20 (catagen), while mutant hair follicles displayed positive staining in the regressing ORS at P20 (catagen) and in the bulge/isthmus and hair germ region at P22 (telogen) and P24 (early anagen), as revealed by quantitative analysis (FIG. 2, B). The absence of apoptosis in the Pofut1/Tgfb3-Cre hair bulb at P30 indicated that the size reduction in the mutant hair bulb is not due to increased apoptosis. In sum, Pofut1-deficient hair follicles display dysregulation of proliferation and apoptosis during the hair cycle transition, which may account for the smaller bulge/hair germ seen in Pofut1/Tgfb3-Cre mice.

Example 3: Abrogation of Notch Signaling Resulted in DNA Damage Response and a Paucity of DNA Repair Machinery in Hair Follicle Lineages The delayed anagen re-entry and dysregulation of proliferation/apoptosis during the hair cycle transition seen in Pofut1/Tgfb3-Cre mice prompted us to examine whether Notch signaling loss leads to certain stress responses, such as DNA damage response (DDR) or cell senescence, in mutant hair follicles.

Figure 3:
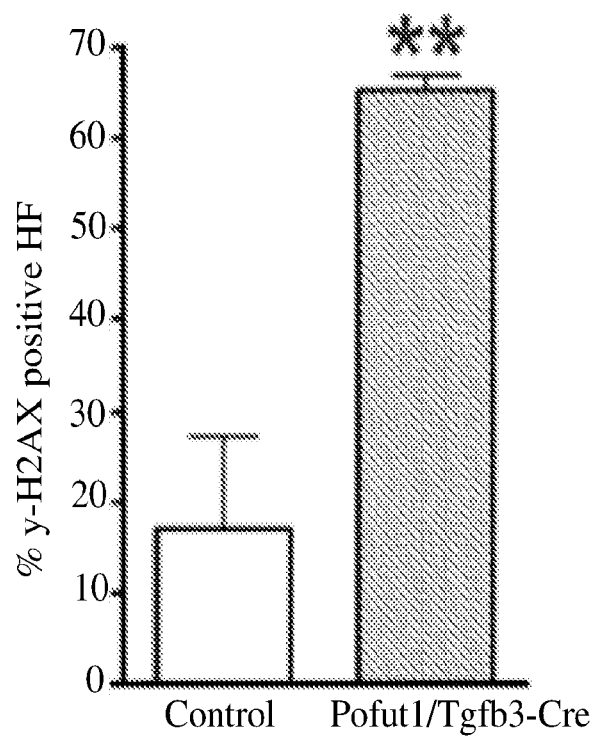
FIG. 3 is a graph showing quantification of γ-H2AX foci in hair follicles from control and Pofut1/Tgfb3-Cre mice. Back skin sections of control and Pofut1/Tgfb3-Cre mice at P22 were immunostained for γ-H2AX. Double-strand DNA-damage foci (γ-H2AX-positive) were detected in the nuclei of mutant follicular cells. The bar graph shows the percentage of γ-H2AX positive hair follicles (mean+/−s.d.) in over 50 fields at 20× magnification from three independent control and mutant pairs. **:P<0.01.

For senescent-associated β-galactosidase assay, frozen sections were fixed in 0.2% paraformaldehyde on ice for 20 min and stained for β-galactosidase activity using X-gal following standard procedure. Sections were counterstained with eosin after X-gal staining. The senescence-associated β-gal staining assay did not reveal cells in hair follicular lineages undertook cell senescence. However, we observed more γ-H2AX foci in Pofut1/Tgfb3-Cre follicular cells than in control follicular cells, suggesting an increase in DNA double-strand break (DSB) signals (FIG. 3).

Next, we explored whether DNA damage signal triggers the cell cycle checkpoint in mutant hair follicle stem cells. Bulge (CD34$^+$CD49f$^{hi}$) keratinocytes from control and Pofut1/Tgfb3-Cre mice at P22 were FACS-isolated and analyzed for gene expression of a panel of pro-apoptotic genes, cell cycle regulators, and DNA repair genes by qRT-PCR. The epidermis was harvested from the dorsal skin by dispase, and single cell suspension of keratinocytes was processed for FACS. Bulge keratinocytes isolated by a FACS were sorted directly into TRIzol reagent. Total RNA was isolated by the RNeasy Mini Kit (Qiagen) according to the manufacturer's protocol. The RNA quality and concentrations were measured by an Agilent 2100 Bioanalyzer (Agilent Technologies, Santa Clara, Calif., USA).

To obtain sufficient amount of samples for qRT-PCR analysis, total RNA isolated from bulge keratinocytes (~200 ng from 10$^5$ cells) was amplified by the RiboMultiplier sense-RNA Amplification Kit (Epicentre Biotech.). Equal RNA amounts (~2 µg) were used to synthesize cDNA with the Transcriptor Reverse Transcriptase (Roche) and oligo-dT primers following the manufacturer's instructions. Real-time PCR was conducted using an ABI 7500 Real-Time PCR system (Applied Biosystems, Foster City, Calif., USA) with FastStart Universal Probe Master (Rox, Roche) and probe/primer sets (Roche Universal Probe or Applied Biosystems Assay-on-Demand) designed to span over gene-specific exon-exon boundaries. Samples were analyzed by SDS Software v1.4 and normalized to the expression of the housekeeping gene ribosomal protein L7 (Rp17) or hypoxanthine-guanine phosphoribosyltransferase (Hprt-1). The number of cycles needed to reach the crossing point (Ct) for each sample was used to perform the relative quantitative analysis with the 2-ΔΔCP method. Gene-specific universal probe numbers and primer sequences are available upon request.

Figure 4:
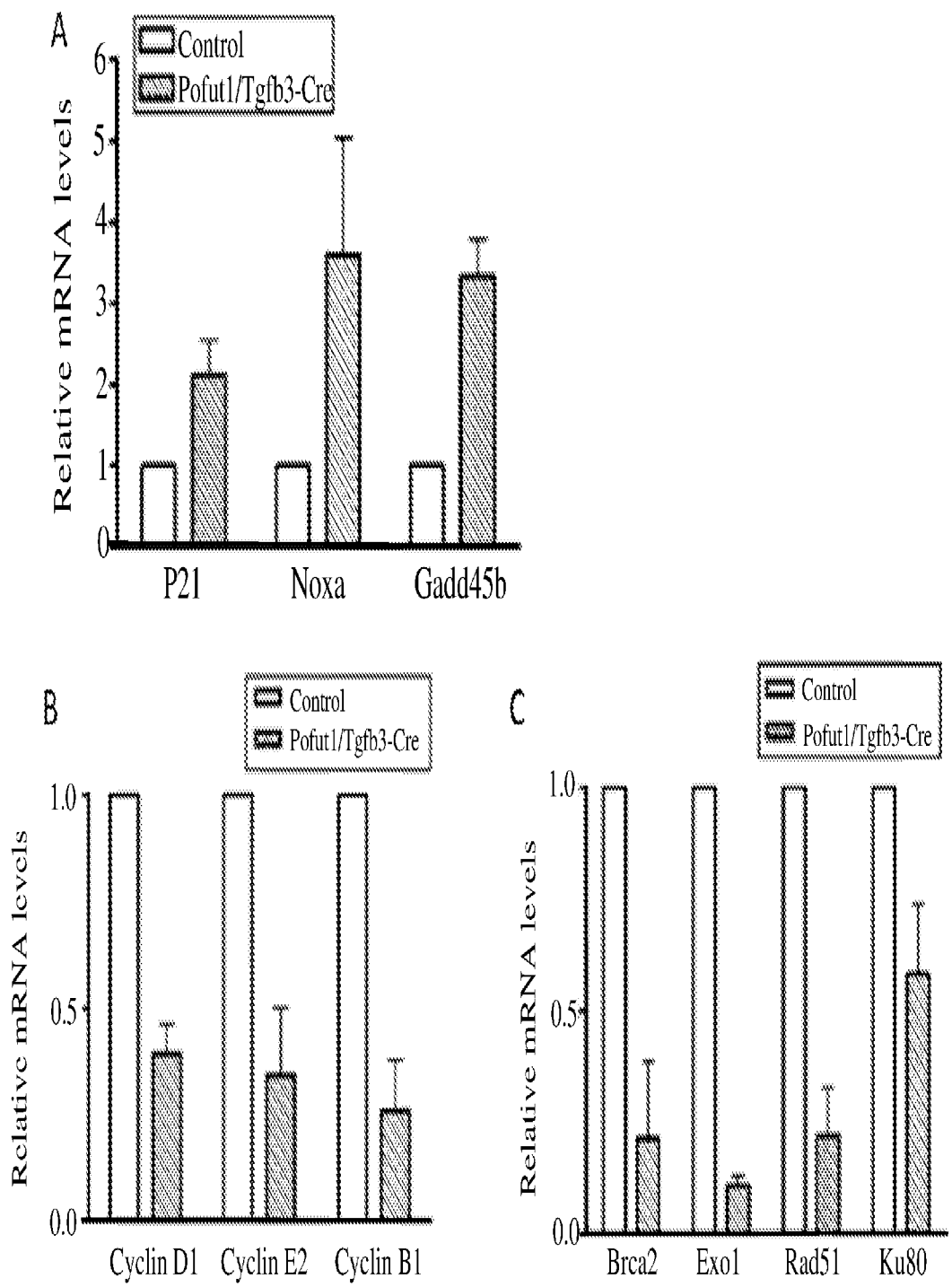
FIGS. 4A-4C are a set of graphs showing qRT-PCR analysis of a selected set of (A) p53 target genes, (B) cyclin genes, and (C) DNA repair genes in bulge keratinocytes isolated from control and Pofut1/Tgfb3-Cre mice. The bar graphs show mRNA levels relative to their corresponding controls (mean+/−s.d., n>3).

As shown in FIG. 4, we observed a modest increase of p21 and a greater increase of Noxa and Gadd45b expression levels in mutants, while expression levels of CyclinD1, CyclinE2, and CyclinB1 were decreased in mutants. Interestingly, we found downregulation of DNA repair genes in homologous recombination and non-homologous end-joining pathways in mutants, including Brca2, Rad51, Ku80, and Exo1. These data suggest that Notch signaling loss in hair follicle lineages leads to increased expression of pro-apoptotic genes, a paucity of DNA repair machinery, and induction of cell cycle checkpoints.

Figure 5:
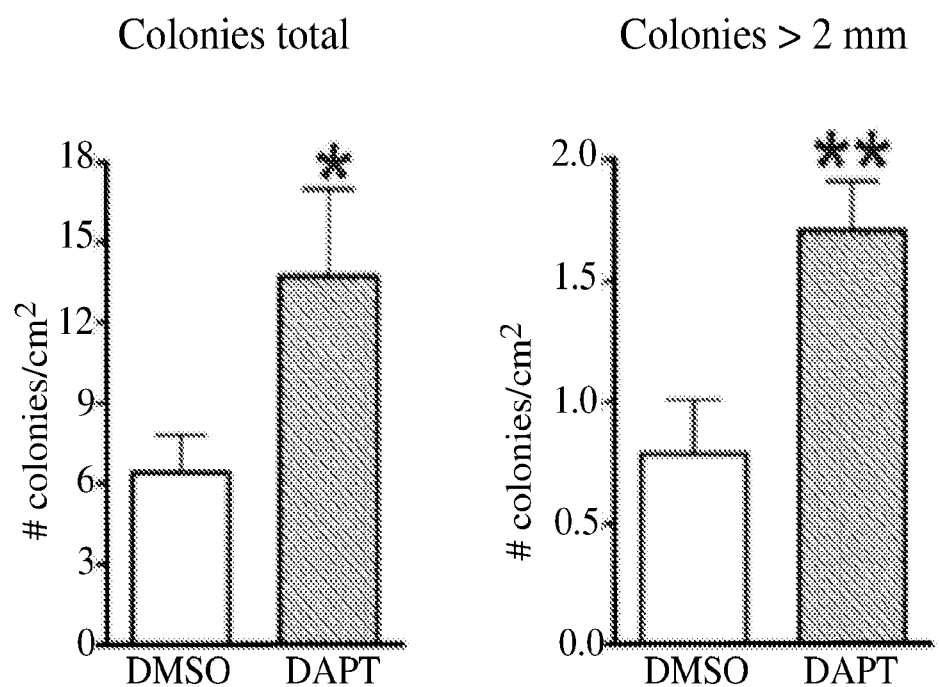
FIG. 5 is a graph showing quantification of a colony forming assay on sorted CD34+α6+ keratinocytes in the absence or presence of DAFT. Equal numbers of sorted CD34±α6+ keratinocytes from 8-week-old wild type mice were cultured with feeders and treated with either DMSO as a vehicle control or 10 μM DAFT for 7 days. The graph shows the number of colonies per square cm (mean+/−s.d., n=3). P<0.05, **:P<0.01.

We investigated whether the DSB signal seen in Pofut1/Tgfb3-Cre hair follicles was caused by aberrant cell proliferation, which has been reported in the case of oncogene-induced DNA damage checkpoint responses. To test this hypothesis, bulge keratinocytes were isolated from 8 weeks old wild type mice by FACS and cultured in the absence or presence of a γ-secretase inhibitor DAPT (Notch signaling inhibitor). Significantly, we observed increases in both the numbers and the size of colonies in DAPT-treated bulge keratinocyte cultures when compared with DMSO-treated bulge keratinocyte cultures (FIG. 5). Our data suggest that Notch signaling loss in the bulge stem cells results in aberrant cell proliferation and such a replication stress may induce DDR followed by cell death.

Example 4: Ablation of Notch Signaling Effector Hes1 in the Murine Epidermis Causes a Defect in the Anagen Initiation and Smaller Hair Bulbs We have demonstrated that ablation of Notch signaling in the hair follicular lineage resulted in a delay in anagen re-entry and increased DNA damage response in the hair follicle stem cells. We further explored the specific role of Hes1, a major target gene of Notch signaling, in the hair follicle cycle. We crossed the Hes1 fx/fx mice to K14-Cre mice and the resulting [Hes1$^{fx/fx}$; K14-Cre] mice (hereafter referred as Hes1eKO mice) were born without any overt phenotype. K14-Cre mice were tested for the gene recombination pattern in the epidermis using the surrogate Rosa26-LacZ reporter mice, and we confirmed that K14-Cre induces gene recombination in the entire layers of the epidermis. RT-qPCR of Notch downstream effectors Hes1, Hes5, and Hey1 in the Hes1eKO epidermis revealed that Hes1 and Hey1 gene expression is significantly decreased and Hes5 gene expression remained comparable when compared with control epidermis (FIG. 6, A).

Figure 6:
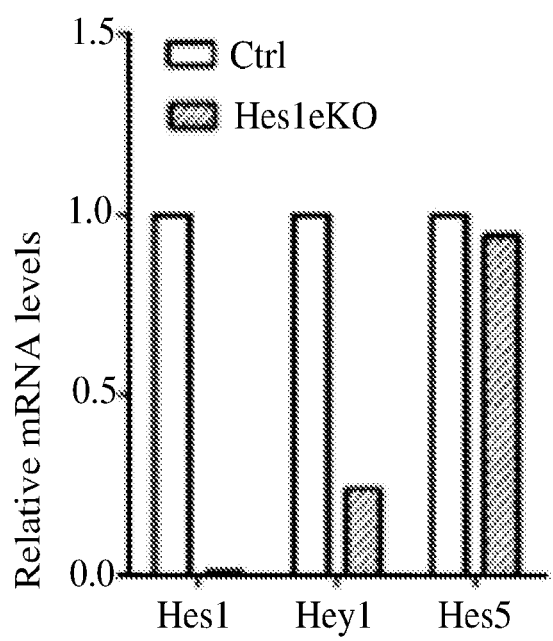
FIGS. 6A-6B show data demonstrating that Hes1 deletion using K14-Cre deleter line caused a delay in anagen initiation during normal morphogenesis. (A) A surrogate reporter Rosa-Lack line was used to confirm the recombination pattern of K14-Cre, A back skin section of [K14-Cre+/wt; Rosa-LacZ+/wt] mice was stained with X-gal. The graph shows quantitative real-time PCR analysis of the expression levels of Hes1, Hes5, and Hey1 in the back skin epithelium of Hes1eKO vs. control mice. (B) The illustration shows the two synchronous hair cycles in mice after birth. Different hair cycle stages within the two hair cycles are coordinated with age.
Figure 6:
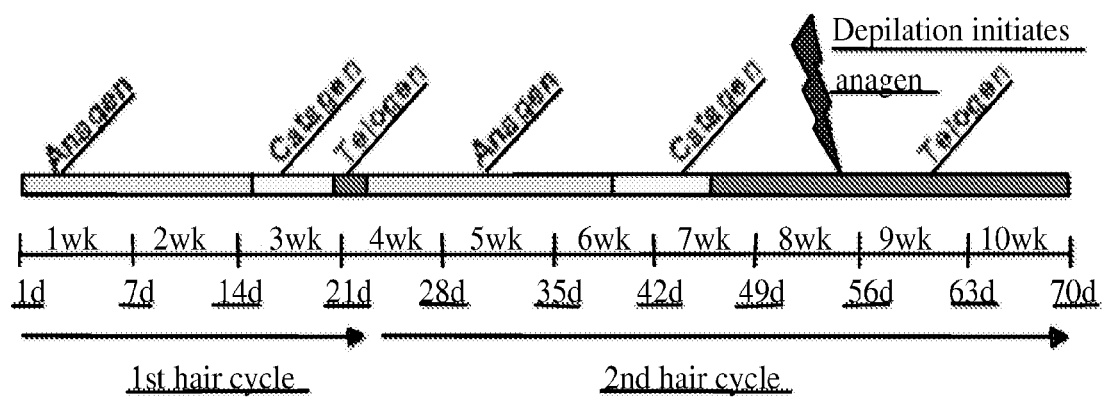

Owing to an important role of Notch signaling in the complete morphogenesis of hair follicles (HFs), we examined the gross phenotype of the back skin at different stages of postnatal hair cycle (FIG. 6, B). Mouse back skin loses pigmentation when HFs are in telogen phase (pink color), while the color of the back skin becomes dark when HFs are in anagen phase (black color). Hair coat of control littermate and Hes1eKO mice were shaved at P20 and it appeared to take longer for the back skin color to turn black in Hes1eKO mice than in control littermate mice. The hair coat of Hes1eKO mice still grew back and there was no overt difference between control and Hes1eKO mice at P35. Mice were then shaved at P42 (catagen) to monitor telogen stage at the back skin, and the shaved area of both control and Hes1eKO mice remained pink at P56 (second telogen), suggesting that HFs of both control and Hes1eKO mice went into telogen.

We then examined back skin samples of control and Hes1eKO mice collected at different hair cycle stages using histological analysis (H&E staining). During the first anlagen (P14) and catagen (P19) phases, there was no discernible difference between Hes1eKO HFs and control HFs. Interestingly, during the second anagen (P20-P24), Hes1eKO HFs appeared to display smaller hair germ compared with control HFs. At late anagen (P28), Hes1eKO hair bulbs were significant smaller than that of the control HFs. At the end of anagen (P35), Hes1eKO hair bulbs were still smaller than that of control HFs. Both of the Hes1eKO and control HFs regressed in catagen (P42) and they displayed telogen morphology in the second telogen (P56), with bulge region close to derma papillae. It is recognized that hair plucking of the telogen HFs will stimulate the anagen re-entry (Muller-Rover S et al., J Invest Dermatol 117:3-15, 2001).

Then a wax-depilation was performed on the back of control and Hes1eKO mice at P56, and back skin samples were harvested from the depilation area of Hes1eKO mice 8 days after depilation. Histological analysis revealed that Hes1eKO hair follicles have smaller hair bulbs than control hair follicles. These data suggest that the HFs of Hes1eKO mice have a defect in the anagen initiation and developed smaller hair bulbs.

Example 5: the Defect in Anagen Initiation of Hes1eKO Hair Follicles is Possibly Due to Imbalanced Activating and Inhibitory Signals of Hair Growth Next, the anagen initiation defect seen in Hes1eKO HFs was analyzed. Control and Hes1eKO HFs at early anagen (P24) were doubly immunostained for P-cadherin (hair germ marker) and Ki67 (proliferative marker), and we observed that Hes1eKO HFs had a decreased cell proliferation in the hair germ in early anagen.

Emerging evidences have shown that anagen initiation is controlled by the balance of activating and inhibitory signals, in which the strength of Wnt signaling (activating) is increased by downregulation of BMP signaling (inhibitory) mediated, at least in part, by TGF-β signaling (Lin H Y, Yang L T. Dev Biol 373:394-406, 2013). We therefore examined signaling pathways of Wnt, BMP, and TGF-β in back skin sections of control and Hes1eKO mice by performing immunostaining of β-catenin, phosphor-Smad1/5/8, and phospho-Smad2/3.

Figure 7:
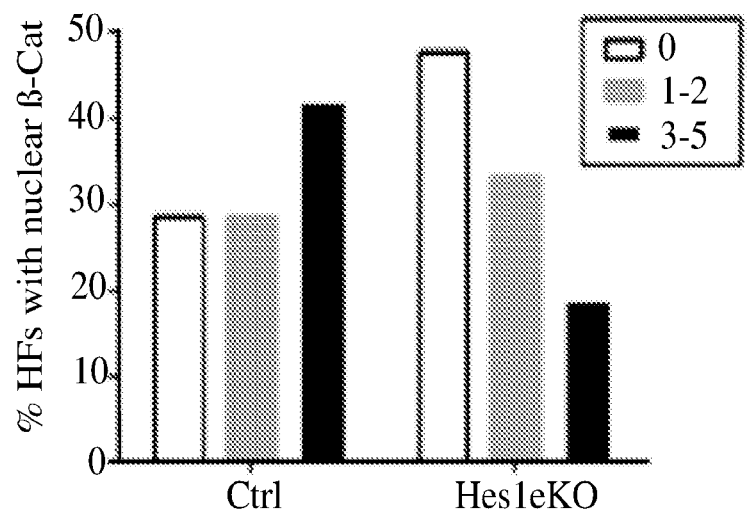
FIGS. 7A-7B are a set of graphs showing that delay in anagen initiation of Hes1-deficient hair follicles may be due to imbalanced activating and inhibitory signals of hair growth. (A) Back skin sections of control and Hes1eKO mice were immunostained for β-catenin. Quantitation of nuclear β-catenin staining is shown in the bar graph. n>30 HFs from two independent control and mutant pairs. (B) Back skin sections of control and Hes1eKO mice were immunostained for phosphor-Smad1/5/8, and quantification of % HF with positive staining is depicted by a bar graph. n>30 HFs from two independent control and mutant pairs.
Figure 7:
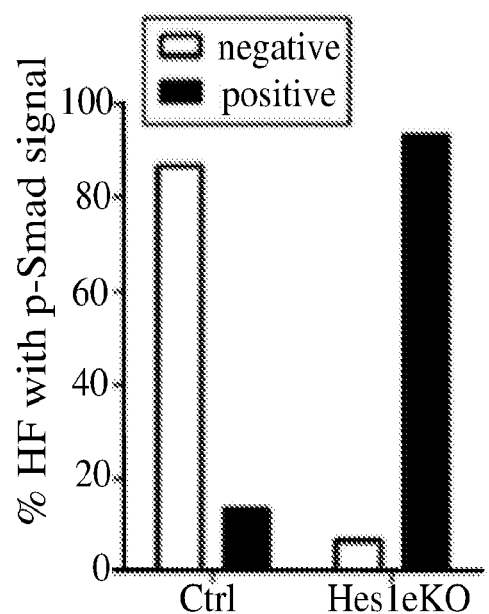

Our quantitative analysis showed that hair germs of Hes1eKO HFs displayed less nuclear β-catenin signals (Wnt signaling) than that of control HFs (FIG. 7, A); control HFs displayed less phospho-Smad1/5/8 signals (BMP signaling) as well as more phospho-Smad2/3 signals (TGF-β signaling) than that of Hes1eKO HFs (FIG. 7, B). These data suggest that Hes1eKO HFs were less activated than control HFs, and that Hes1 may control the threshold of bulge stem cell activation in response to anagen-promoting signals.

We also confirmed that the delay in anagen initiation of Hes1eKO HFs is due to neither apparent loss of HFSCs nor increased cell death in the bulge region, as evidenced by comparable immunostaining of hair follicle stem cell markers CD34 (primary antibody 1:100, eBioscience), Sox9 (primary antibody 1:100, Santa Cruz), and NFATc1 (primary antibody 1:150, Santa Cruz), and by lack of TUNEL staining in control and Hes1eKO HFs. TUNEL assays were conducted using the DeadEnd Fluorometric TUNEL system (Promega) following the manufacturer's instructions. Positively stained cells were counted manually in a defined area of the tissues. Statistical analyses were done in serial sections from two to three independent controls and mutant pairs using a Student's t-test, and a P-value less than 0.05 was considered to be significant.

Figure 8:
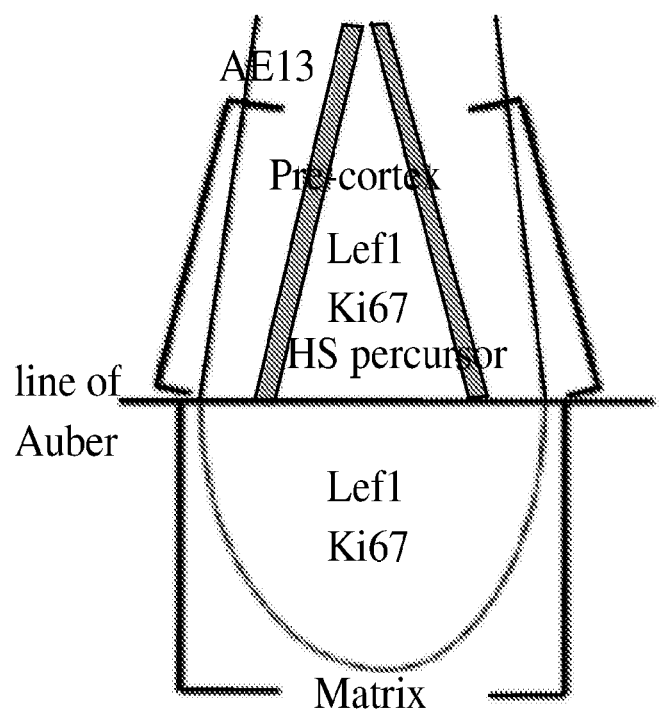
FIG. 8 is a schematic illustration of the hair bulb containing the matrix (Lef1+ and Ki67+, below the line of Auber) and hair shaft precursor cells (Lef1+ and Ki67+, above the line of Auber and within the AE13 marker).

Example 6: Anagen Hair Bulb Defects in Hes1eKO Hair Follicles May be Caused by a Developmental Delay in Morphogenesis To investigate the hair bulb defects of Hes1eKO HFs, we first analyzed the proliferative status in both the hair bulb and the hair shaft precursors. Also see FIG. 8. Cell proliferation analysis was done by either immunostaining for BrdU incorporation using a Cell Proliferation kit (Amersham) or Click-iT EdU Alex Fluor 594 Imaging kit (Thermo Fisher Scientific) following the manufacturers' protocols.

Figure 9:
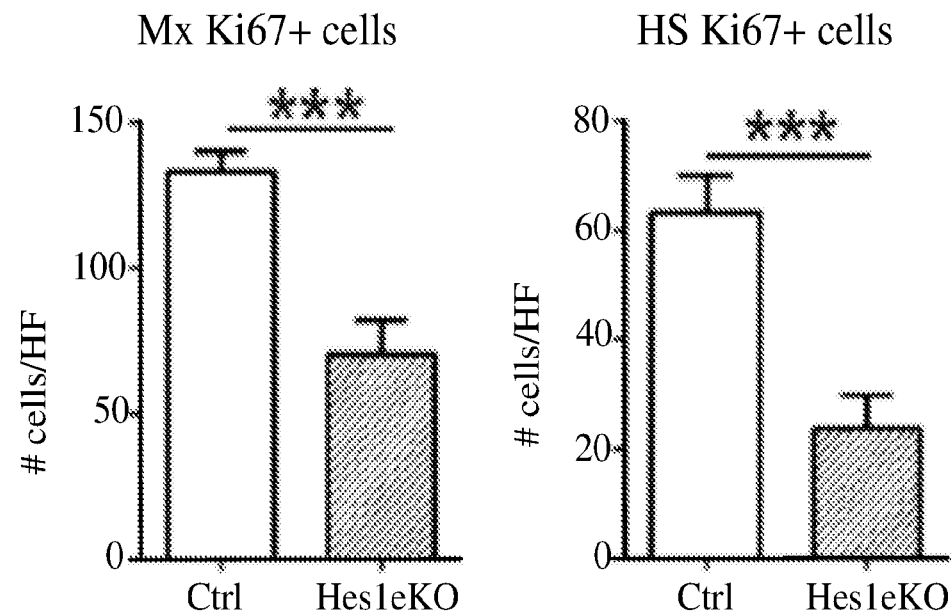
FIGS. 9A-9B are a set of graphs showing that the smaller hair bulb in Hes1-deficient hair follicles is possibly caused by a developmental delay in morphogenesis. (A) Back skin sections of control and Hes1eKO mice were double immunostained for AE13 and Ki67. Quantitation of cell proliferation in the matrix and hair shaft precursors is shown in the bar graphs (mean+/−s.d., n>30 HFs from two independent pairs). *: P<0.001, (B) Back skin sections of control and Hes1eKO mice were double immunostained for AE13 and Lef1. Quantitation of Lef1+ cells in the matrix and hair shaft is shown in the bar graphs (mean+/−s.d., n>30 HFs from two independent pairs). *: P<0.001.
Figure 9:
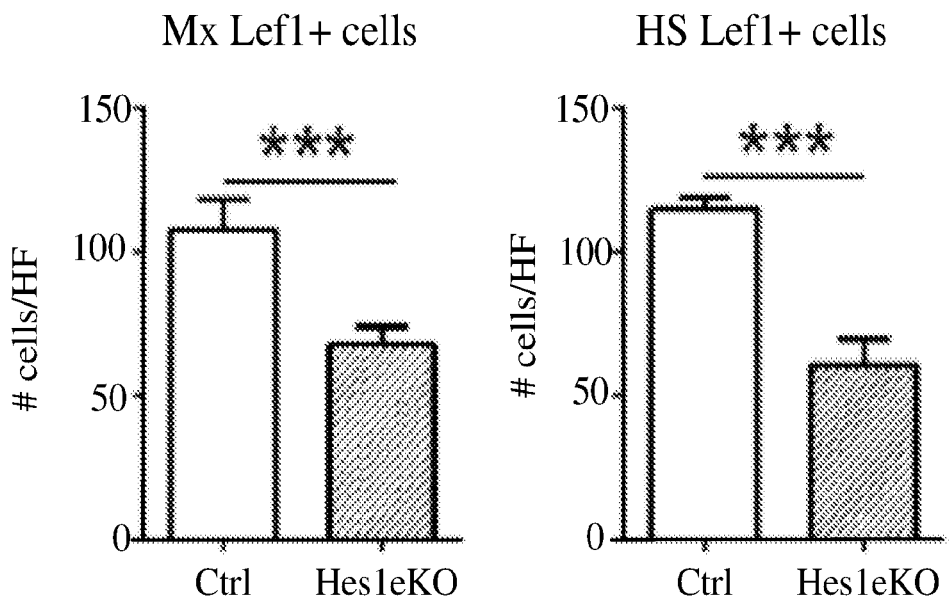

As evidenced by Ki67 staining (cell proliferative marker), the matrix cells in control HFs displayed more cell proliferation than that of Hes1eKO HFs. In addition, the hair shaft precursors are less proliferative in Hes1eKO HFs than that of control HFs (FIG. 9, A). The hair matrix and hair shaft precursor, indicated by Lef1+ cells, were also examined in control and Hes1eKO HFs. We found that Hes1eKO HFs have fewer matrix cells and hair shaft precursors than control HFs, as revealed by quantitative analysis of Lef1 staining (FIG. 9, B). We excluded the possibility that increased cell death is the underlying cause, as evidenced by TUNEL staining results of control and Hes1eKO mice second synchronous anagen, catagen and telogen phase.

Figure 10:
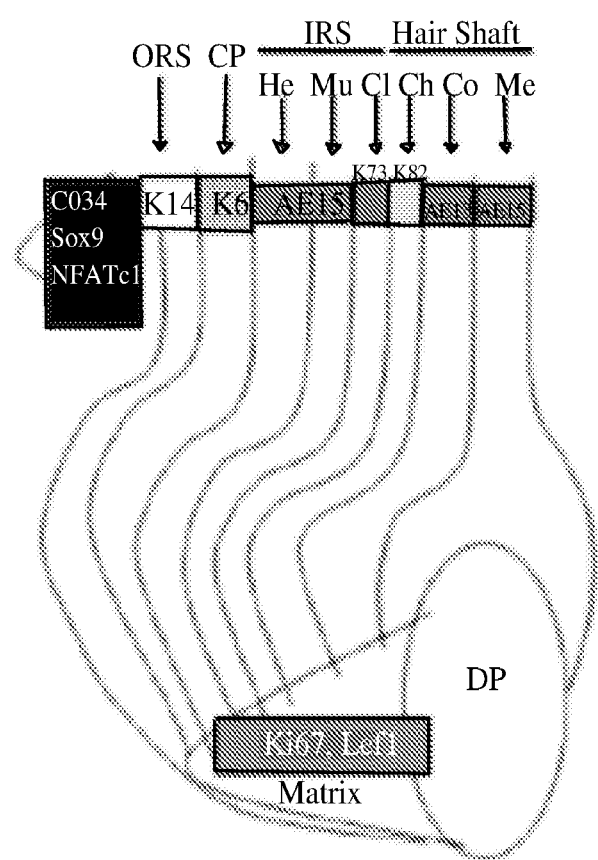
FIG. 10 is an illustration of the hair keratin marker in distinct cell layer of the hair follicle. ORS, outer root sheath; CP, companion layer; He, Henle layer; Hu, Huxley layer; Ci, cuticle of the IRS; Ch, cuticle of the hair shaft; Co, cortex of the hair shaft; Me, medulla of the hair shaft.

To examine whether Hes1 deletion in the hair follicular lineages causes any hair structure defect (FIG. 10), we analyzed hair keratin markers K6 (companion layer), AE15 (IRS He, Hu, and hair shaft Me), AE13 (hair shaft Co), K82 (hair shaft Ch), and K73 (IRS Ci) at P29 (mid-anagen) and P35 (late anagen). K6 staining revealed that both control Hes1eKO HF have companion layers. Interestingly, AE15 (1:100, Santa Cruz) staining revealed that Hes1eKO HFs lack the medulla layer of the hair shaft at P29; AE13 (1:100, Abcam) staining revealed that Hes1eKO HFs have developed a shorter hair shaft than that of control HFs at P29. K82 (1:100, Abnova) and K73 (1:150, biorbyt) staining also revealed a decreased formation of cuticle layers of both the hair shaft and IRS in Hes1eKO HFs at P29 compared with control HFs. Remarkably, hair shaft medulla (AE15+) of Hes1eKO HFs started to appear, and the AE13+, K82+, and K73+ cell layers of Hes1eKO HFs extended their length at P35. Our data indicate that Hes1-deficient hair follicles could regenerate hair follicle lineages in anagen but they displayed a significant delay in morphogenesis, as indicated by slower development of IRS and hair shaft cell layers during anagen.

Example 7: Hes1-Deficient Hair Follicle Stem Cells do not Maintain their Self-Renewal Capability in In Vitro Colony Forming Assays HFSCs preserve self-renewal capability and they can continuously proliferate in vitro after several passages, a characteristic of stemness. Since less activated telogen HFs were observed in Hes1eKO mice, we investigated the colony forming ability (CFA) of Hes1eKO HFSCs in a serial passage experiment.

HFSCs were FACS-sorted from 8 week-old control and Hes1eKO mice. Equal numbers of isolated HFSCs (~5000) were seeded onto mitomycin C-treated swiss 3T3 fibroblast and cultured for three serial passages. We observed that Hes1eKO HFSCs initially displayed a higher CFA than control HFSCs; however, the CFA of Hes1eKO HFSCs decreased significantly in the second and third passages when compared with control HFSCs. These data suggest that Hes1-deficient HFSCs are more like progenitor cells and gradually lose their stemness.

Example 8: Preparation and Application of Soluble Notch Ligand Delta-Fc

Immobilized or IgG-clustered form of Notch soluble ligand Delta1-Fc has been shown to activate Notch signaling (Hicks C et al., J Neurosci Res 68:655-667, 2002). To demonstrate that Notch signaling plays a role in the maintenance of HFSCs, we constructed a soluble ligand Delta1-Fc and used it to activate Notch signaling during HFSC colony forming assay.

We made Delta1-Fc fusion protein containing mouse Delta1 extracellular domain (a.a. 1-530) and the Fc region of human IgG2. 293T cells were either mock transfected or transfected with Delta1-Fc expression construct, and immunoblotting with an HRP-conjugated goat-anti-human Fc antibody confirmed the expression of Delta1-Fc as a 90 kDa protein in culture supernatant. To construct the Notch soluble ligand, the cDNA sequence corresponding to a.a. 1-530 of mouse Delta1 was PCR-amplified and cloned into the EcoRI and Bgl II site of pFUSE-hIgG2-Fc vector (hereafter named Delta1-Fc plasmid). The resulting Delta-Fc fusion proteins were produced by transfecting 293T cells with Delta1-Fc plasmid. After transfection, culture medium of 293T cells was changed to low calcium DMEM/F12 (0.07 mM $Ca^{2+}$, 1% FBS) 16 hour post transfection. Supernatant was collected 4 days after transfection and centrifuged to get rid of the cell debris. To immobilize the Delta1-Fc protein by antibody clustering, goat anti-human IgG Fc IgG was mixed with Delta1-Fc in a molar ration of 1:2 (Delta-Fc: IgG) in E-Media (Nowak J A et al., Methods Mol Biol 482:215-232, 2009) on a rotator for 30 min at RT. Then, the clustered Delta1-Fc protein was applied in the hair follicle stem cell cultures at 0.4 µg (3.12 nM)/well in 12 well plates.

Figure 11:
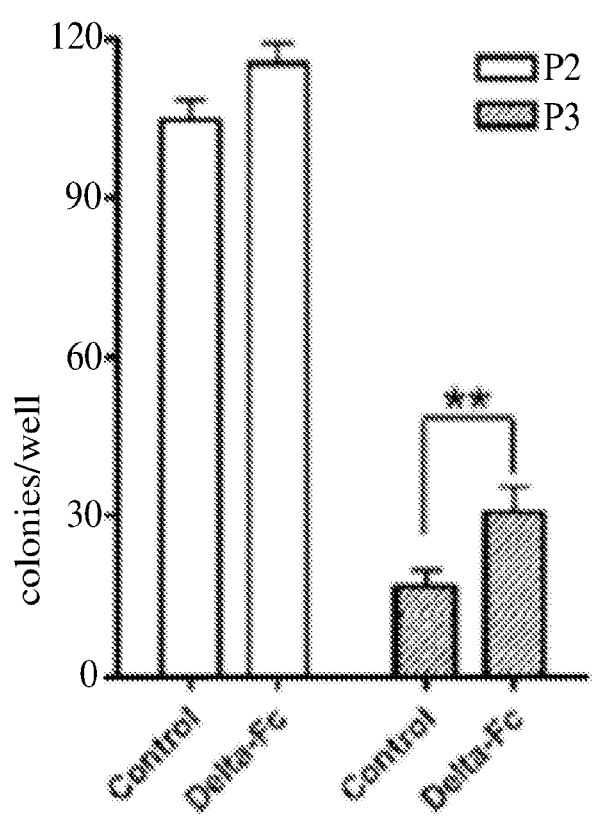
FIG. 11 is a graph showing quantitation of serial colony forming assays in the absence or presence of Delta1-Fc. (mean+/−s.d., n=3). **:P<0.01. P2, passage 2; P3, passage 3.

Next, the effect of clustered Delta1-Fc protein on bulge stem cell self-renewal was tested. HFSCs were isolated and their CFA was determined by serial passage in the absence or presence of clustered Delta1-Fc. We found that Delta-Fc can maintain the CFA of HFSCs after three passages, while in its absence HFSCs appeared to gradually lose their ability to self-renew, as evidenced by quantification of the CFA results (FIG. 11).

Example 9: Hes1-Deficient Hair Follicle Stem Cells Fail to Sustain the Long-Term Regeneration in a Repetitive Depilation In Vivo Assay Given that Hes1-deficient HFSCs displayed less self-renewal capability than control HFSCs in in vitro colony forming assays, we applied an in vivo assay devised to test stem cell self-renewal and long-term regeneration (Chen T et al., Nature 485:104-108, 2012). To challenge the HFSCs for their long-term regeneration capability, we repeatedly depilated the hair coat of control littermates and Hes1eKO mice and monitored the HF regeneration for 4 rounds.

Figure 12:
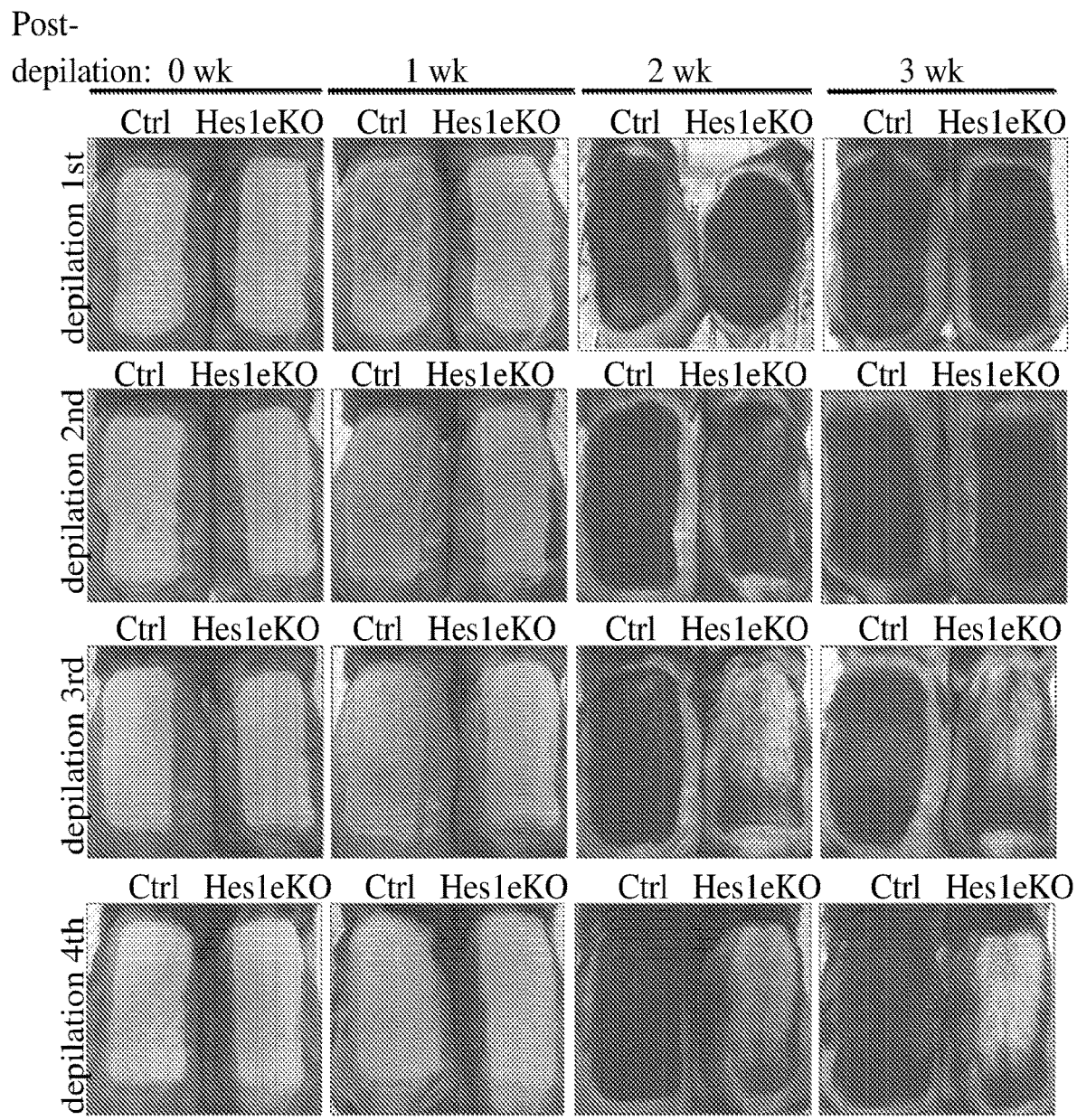
FIG. 12 is a set of photographs showing that deletion of Hes1 in the epidermis using K14-Cre resulted in delayed hair growth and thinning of hair coat after repetitive depilation. The back skin of control littermate (Ctrl) and Hes1 conditional knockout mice (Hes1eKO) was shaved and depilated (hair plucking) at postnatal day 50 (P50) for 4 consecutive times with a three-week interval. Hair plucking promotes the hair follicle to initiate a new hair cycle. It normally takes 3 weeks for the hair follicles to regenerate after hair plucking, undergoing one round of anagen-catagen-telogen hair cycle. Photographs of the back coat were taken from control and Hes1eKO mice at 0 week, 1 week, 2 week, and 3 week after depilation.

Hair plucking removes the club hair (old hair) along with the adhered inner bulge cells which maintain the HFSC quiescence. After depilation, the remaining viable HFSCs become activated and enter into a new hair cycle. We noted that control HFSCs could replenish the coat hair after each round of depilation-induced hair regeneration. In contrast, Hes1eKO HFs displayed a gradual thinning of hair coat and a reduction in the hair regeneration after repetitive depilation, suggesting that Hes1eKO HFSCs do not maintain their long-term regeneration and exhibit premature aging in this in vivo stress test (FIG. 12). Our data suggest that Hes1 may participate in the HFSC maintenance during long-term regeneration.

During the anagen initiation, the hair germ is expended at the first place to form the hair follicle lineages, and HFSCs then proliferate to replenish the progenitors (hair germ) as well as to self-renew themselves (bulge) (Greco V et al., Cell Stem Cell 4:155-169, 2009).

Figure 13:
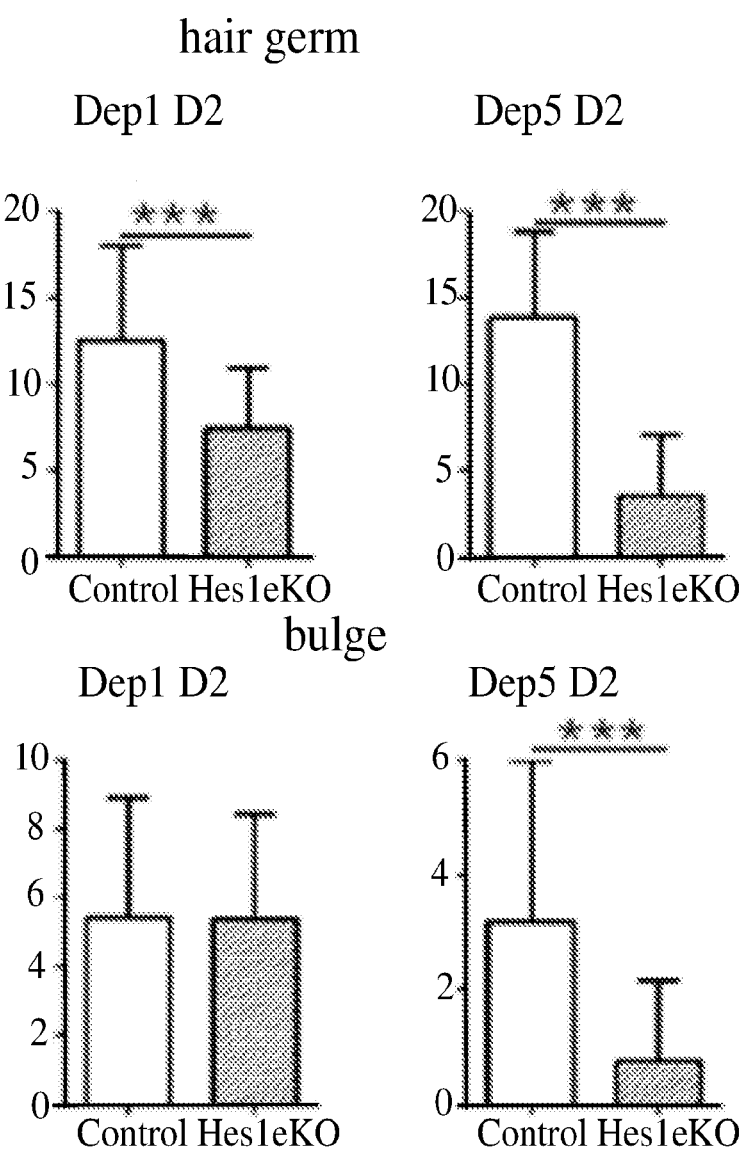
FIG. 13 is a set of graphs showing cell proliferation in both the hair germ and bulge at day 2 post depilation (1 and 5 times). The back skin sections of control and Hes1eKO mice, repetitively depilated for either 1 or 5 times, were processed for cell proliferation assays.

To characterize the mechanism of premature hair loss after repetitive depilation in Hes1eKO mice, we first examined the proliferation status of hair germ and bulge, which reflects the capability of HFSCs for progenitor replenishment and stem cell self-renewal, respectively (FIG. 13).

Figure 14:
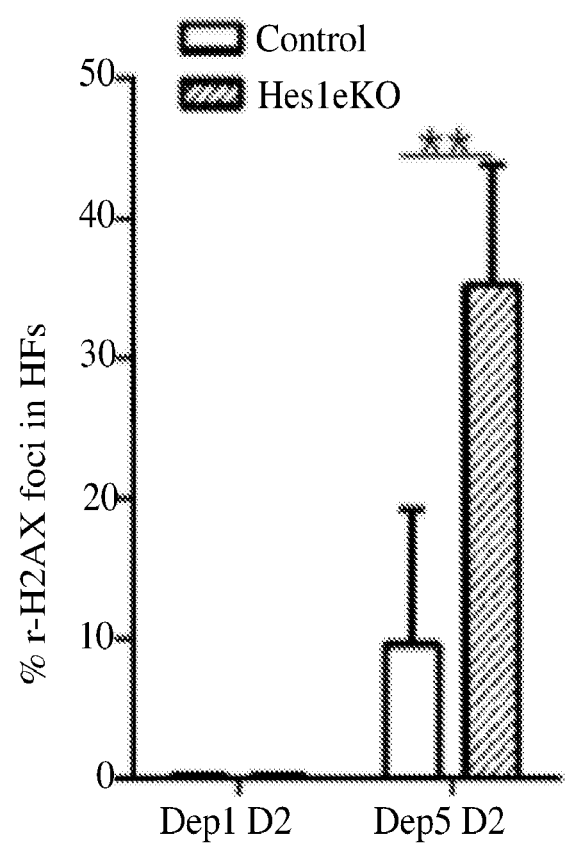
FIG. 14 is a graph showing quantification of hair follicles with γ-H2AX foci. The back skin sections of control and Hes1eKO mice, repetitively depilated for either 1 or 5 times, were processed for immunostaining.

Immunostaining of CD34 and EdU incorporation assays on control and Hes1eKO hair follicles revealed a gradual loss of hair germ proliferation after repetitive depilation (compared day 2 after the first depilation and that of the fifth depilation). While HFSCs of control and Hes1eKO mice can self-renew at a comparable level at the first depilation, HFSCs of Hes1eKO mice failed to maintain their self-renewal capability after 5 rounds of depilation. As DNA damage accumulation was found as a hallmark of aging HFs, we also examined the DNA damage response (DDR) in Hes1eKO HFs. We found that Hes1eKO HFs have a significant increase in γ-H2AX foci formation (DNA double strand break marker) after repetitive depilation (FIG. 14), which indicates that sustained DDR may account for, at least in part, the genomic stress leading to premature hair loss observed in Hes1eKO mice after repetitive depilation.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. A method of treating a hair loss condition, comprising administering locally a Notch signaling pathway activator to an area affected with hair loss of a subject in need thereof, wherein the Notch signaling pathway activator is a soluble Notch ligand.

2. The method of claim 1, wherein the soluble Notch ligand is selected from the group consisting of Jagged1, Jagged2, Delta1, and Delta4.

3. The method of claim 1, wherein the hair loss condition is male-paste m hair loss, female-pattern hair loss, alopecia areata, anagen effluvium, or telogen effluvium.

4. The method of claim 1, wherein the activator is administered topically.

* * * * *